United States Patent [19]

Makino et al.

[11] Patent Number: 4,948,788

[45] Date of Patent: Aug. 14, 1990

[54] COMPOSITION FOR INJECTION OF ACTIVE TYPE VITAMINS $D_3$

[75] Inventors: Yuji Makino; Yoshiki Suzuki, both of Hino, Japan

[73] Assignee: Teijin Limited, Osaka, Japan

[21] Appl. No.: 904,125

[22] Filed: Sep. 5, 1986

[30] Foreign Application Priority Data

Sep. 5, 1985 [JP] Japan .................................. 60-194734

[51] Int. Cl.$^5$ ............................................. A61K 31/59
[52] U.S. Cl. ..................................................... 514/167
[58] Field of Search ......................................... 514/167

[56] References Cited

U.S. PATENT DOCUMENTS

| | | | |
|---|---|---|---|
| 4,004,003 | 1/1977 | Babcock | 514/167 |
| 4,190,666 | 2/1980 | Cherkofsky | 514/398 |
| 4,308,264 | 12/1981 | Conway et al. | 424/236 |
| 4,340,592 | 7/1982 | Adibi | 514/19 |
| 4,501,738 | 2/1985 | Yamato et al. | 514/167 |
| 4,530,836 | 7/1985 | Yanaihara | 514/16 |
| 4,665,057 | 5/1987 | Nelson | 514/546 |
| 4,729,895 | 3/1988 | Makino et al. | 424/465 |
| 4,740,373 | 4/1988 | Kesselman | 514/167 |

FOREIGN PATENT DOCUMENTS

2036890 12/1970 France.

OTHER PUBLICATIONS

Makino, Chem. Abs. 107, 141117h (1987).
Nippon, I, Chem. Abs. 99, 146124j (1983).
Nippon II, Chem. Abs. 102, 226051d (1985).
Nippon, Chem. Abs. 99, 146124j (1983).
Abstract for JP 58-116413 (1983).
Nippon Oils, Chem. Abs. 102, 226051d (1985).

*Primary Examiner*—Mark L. Berch
*Attorney, Agent, or Firm*—Sughrue, Mion, Zinn, Macpeak & Seas

[57] ABSTRACT

A composition for the injection of active type vitamins $D_3$ comprising a lyophilized product of active type vitamins $D_3$ and an excipient. This composition has good stability of active type vitamins $D_3$ and is effective as an injection preparation.

3 Claims, No Drawings

COMPOSITION FOR INJECTION OF ACTIVE TYPE VITAMINS $D_3$

BACKGROUND OF THE INVENTION

1. Field of the Invention

The present invention relates to a novel composition for the injection of active type vitamins $D_3$. More specifically, the present invention relates to a composition for the injection of active type vitamins $D_3$ comprising a lyophilized product of active type vitamins $D_3$ and an excipient.

2. Description of the Related Art

Active vitamins $D_3$ such as $1\alpha$-hydroxycholecalciferol, $1\alpha,25$-dihydroxycholecalciferol, $1\alpha,24$-dihydroxycholecalciferol, etc., have functions to accelerate the absorption of calcium through the small intestine and also promote the resorption of calcium from the bone and accordinlgy they are useful as a remedy for treating such diseases as osteoporosis, osteomalacia, rickets, etc.

However, these active type vitamins $D_3$ are all unstable to heat and light, and also susceptible to oxidation, and therefore, a stable preparation thereof is desired.

In the prior art, as the preparations of these active type vitamins $D_3$, preparation forms for oral administration such as soft capsules having active type vitamins $D_3$ dissolved in medium chain fatty acid triglycerides (see Japanese Unexamined Patent Publication (Kokai) No. 53-26316), tablets, hard capsules, etc , comprising compositions of active type vitamins $D_3$ and polyvinylpyrrolidone (see Japanese Unexamined Patent Publication (Kokai) No. 58-206533) are known.

In recent years, the necessity for administering these active type vitamins $D_3$ as injection preparations to patients suffering from cancer, etc., requiring a large amount of active type vitamins $D_3$, old people, or patients to whom oral administration is not adequate because of digestive tract abnormality, bile duct obliteration or stomach ablation, etc., has been recognized.

In the prior art, as the injection preparation of active type vitamins $D_3$, aqueous injection preparations having active type vitamins $D_3$ solubilized together with antioxidants, chelating agents, etc., have been known (c.f. Japanese Unexamined Patent Publication (Kokai) No. 57-144218, which corresponds to U.S. Pat. No. 4308264). However, this method has a cumbersome preparation process, and requires a high technique for the preparation and the stability of the active type vitamins $D_3$ in the aqueous injection preparation is insufficient. Therefore, it cannot be said to be a useful preparation. Accordingly, there is a need to develop an injection preparation of active type vitamins $D_3$ which can be easily prepared and has a good stability.

SUMMARY OF THE INVENTION

Accordingly, the objects of the present invention are to eliminate the above-mentioned disadvantages of the prior art and to provide a composition for the injection of active type vitamins $D_3$ having good stability, which can be easily prepared and is effective as an injection preparation.

Other objects and advantages of the present invention will be apparent from the following description.

In accordance with the present invention, there is provided a composition for the injection of active type vitamins $D_3$, comprising a lyophilized product of active type vitamins $D_3$ and an excipient.

DESCRIPTION OF THE PREFERRED EMBODIMENTS

According to the present invention, the desired composition for the injection of active type vitamins $D_3$ having a good stability of active type vitamins $D_3$ can be provided by lyophillizing active type vitamins $D_3$ and an excipient. This composition can be easily prepared and is effective as an injection preparation.

Examples of the active type vitamins $D_3$ according to the present invention are active type vitamins $D_3$ having a hydroxyl group at the $1\alpha$-position such as $1\alpha$-hydroxycholecalciferol ($1\alpha$-OH-$D_3$), $1\alpha,25$-dihydroxycholecalciferol ($1\alpha,25$-(OH)$_2$-$D_3$), $1\alpha,24$-dihydroxycholecalciferol ($1\alpha,24$-(OH)$_2$-$D_3$), $1\alpha,24,25$-trihydroxycholecalciferol ($1\alpha,24,25$-(OH)$_3$-$D_3$), $1\alpha$-hydroxy-24-oxocholecalciferol, $1\alpha,25$-dihydroxy-24-oxocholecalciferol, $1\alpha,25$-dihydroxycholecalciferol-26,25-lactone, $1\alpha,25$-dihydroxycholecalciferol-26,23-peroxylactone, $26,26,26,-27,27,27$-hexafluoro-$1\alpha,25$-dihydroxycholecalciferol or the like; or active type vitamins $D_3$ having no hydroxyl group at the $1\alpha$-position such as 25-hydroxycholecalciferol (25-OH-$D_3$), 24-hydroxycholecalciferol (24-OH-$D_3$), 24-oxocholecalciferol, 24,25-dihydroxycholecalciferol (24,25-(OH)$_2$-$D_3$), 25-hydroxy-24-oxocholecalciferol, 25-hydroxycholecalciferol-26,23-lactone, 25-hydroxycholecalciferol-26,23-peroxylactone or the like.

Among these active type vitamins $D_3$, $1\alpha$-OH-$D_3$, $1\alpha,25$-(OH)$_2$-$D_3$, $1\alpha,24$-(OH)$_2$-$D_3$, $1\alpha,25$-dihydroxycholecalciferol-26,23-lactone are preferred.

The excipients usable in the present invention may include amino acids, monosaccharides, disaccharides, cellulose derivatives, polyvinyl pyrrolidones, organic acids and inorganic compounds. Examples of amino acids are glycine, arginine, alanine and pharmaceutically acceptable salts thereof, and the like. Monosaccharides and disaccharides may include mannitol, inositol, xylitol, lactose, glucose, and the like. Cellulose derivatives may include sodium carboxymethyl cellulose, methyl cellulose, and the like. Polyvinyl pyrrolidones may include polyvinyl pyrrolidones having a molecular weight of, for example, 1,000 to 700,000, more preferably 2,500 to 500,000. Organic acids may include ascorbic acid, citric acid, and the like. The salts of the organic acids also may be included in the term "organic acid" herein used. Examples of inorganic compounds are sodium hydrogen phosphate, sodium hydrogen carbonate, sodium acetate, and the like. These compounds may be used alone or in any mixtures thereof.

Of these excipients, glycine, arginine, alanine, pharmaceutically acceptable salts thereof, mannitol, inositol and xylitol are preferred.

The composition for injection of the present invention is obtained by lyophilizing these excipients and active type vitamins $D_3$. Lyophilization may be usually carried out in the following manner.

In an aqueous solution of an excipient, active type vitamins $D_3$ are added and sufficiently dissolved therein, followed by lyophilization. As the dissolving liquid for the excipient, it is preferable to use distilled water for injection, physiological saline for injection, Ringer's solution for injection. When the active type vitamins $D_3$ are not sufficiently dissolved in the aqueous excipient solution, a solution of the active type vitamins $D_3$ dissolved in a minute amount of an alcohol such as ethyl alcohol may be added into the aqueous excipient solution or alternatively the active type vitamins $D_3$ may be solubilized by addition of a minute amount of a surfactant into the aqueous excipient solution. In this case, a nonionic surfactant such as polysorbates, polyoxyethylene derivatives, etc., may be preferably used as the surfactant. The excipient may be used in an amount of preferably, 100 to 1,000,000 parts by weight, more preferably 1,000 to 100,000 parts by weight, based on 1 part by weight of the active type vitamins $D_3$. The amount of the dissolving liquid for the excipient may differ slightly depending on the kind of the excipient, but it is ordinarily preferable to use 1 to 10,000 parts by weight based on 1 part by weight of the excipient.

The aqueous excipient solution having active type vitamins $D_3$ dissolved therein preferably should be subjected to sterilizing filtration when carrying out the lyophilization. Lyophilization may be also conducted with the addition of an analgesic, a preservative, a buffer, and the like. The stabilizer to be added may include antioxidants such as sodium pyrosulfite, l-ascorbic acid, and the like, and chelating agents such as EDTA, thioglycollic acid, and the like. Examples of the surfactants may include nonionic surfactants, such as polysorbates, polyoxyethylene derivatives and others. Examples of the isotonic agents are sodium chloride and the like. Examples of the analgesics are benzyl alcohol, xylocaine, procaine, and the like. Examples of the preservatives are paraoxybenzoic acid esters, chlorobutanol, benzalconium chloride, thimerosal, and the like. Examples of the buffering agents are sodium salts of citric acid, acetic acid, phosphoric acid, etc. These stabilizers, surfactants, isotonic agents, analgesics, preservatives, buffering agents, and the like may be also added after lyophilization.

Thus, compositions for the injection of active type vitamins $D_3$ can be obtained. Such compositions can be formed into injection preparations in unit dosage forms by sealing into vials for injection. In this case, the vials should preferably have an internal vacuum or be replaced with an inert gas such as nitrogen, etc. Also, in carrying out lyophilization, the aqueous excipient solution having active type vitamins $D_3$ dissolved therein can be apportioned into vials for lyophilization before lyophilization. In this case, after lyophilization, the vials can be internally vacuumized or replaced with nitrogen gas, sealed with stoppers and used as such for injection preparations in unit dosage forms.

The amount of the active type vitamins $D_3$ to be contained in the injection preparation in unit dosage form can be adequately increased or decreased, but it is usually preferably 0.01 to 10 $\mu$g.

The composition for injection of the present invention is usually sealed into a vial and then dissolved before used. The dissolving liquid may preferably be distilled water for injection, physiological saline for injection, Ringer's liquid for injection, etc.

According to the composition for injection of the present invention, active type vitamins $D_3$ such as $1\alpha$-OH-$D_3$, $1\alpha,25$-$(OH)_2$-$D_3$, $1\alpha,25$-$(OH)_2$-$D_3$-26,23-lactone, etc., can be administered intravenously or subcutaneously to cancer patients, old people, or patients for whom oral administration is not suitable because of digestive tract abnormality, bile duct obliteration, stomach ablation, etc., and the significance of the present invention is great as it provides a new preparation form of active type vitamins $D_3$.

EXAMPLES

The present invention will now be further illustrated by, but is by no means limited to, the following Examples.

EXAMPLE 1

A 1 mg amount of $1\alpha$-OH-$D_3$ was dissolved in 0.1 ml of ethanol (Japanese Pharmacopoeia, i.e., "JP"). This solution was added to a solution of 50 g of glycine dissolved in 1000 ml of distilled water for injection. After stirring, the mixture was filtered through a membrance filter and the filtrate was apportioned each in 1 ml into vials for lyophilization. The vials were lyophilized, filled internally with nitrogen gas, and then stoppered with sterilized rubber stoppers and caps made of aluminum, to obtain powdery injection preparations to be dissolved before use. The injection preparation obtained was found to contain 1 $\mu$g of $1\alpha$-OH-$D_3$ and 50 mg of glycine in one vial.

EXAMPLE 2

A 1 mg amount of $1\alpha,24(R)$-$(OH)_2$-$D_3$ was dissolved in 0.1 ml of ethanol (JP). This solution was added to a solution of 1 g of EDTA, 5 g of sodium ascorbate and 50 g of mannitol dissolved in 1000 ml of distilled water for injection and, after stirring, filtered through a membrance filter. 1 ml of the filtrate was apportioned to each vial for lyophilization. The vials were lyophilized, filled internally with nitrogen gas and then stoppered with sterilized rubber stoppers and caps made of aluminum, to obtain powdery injection preparations to be dissolved before use. The injection preparation obtained was found to contain 1 $\mu$g of $1\alpha,24(R)$-$(OH)_2$-$D_3$, 1 mg of EDTA, 5 mg of sodium ascorbate and 50 mg of mannitol in one vial.

EXAMPLE 3

The same procedure as in Example 2 was repeated by use of $1\alpha$-$25$-$(OH)_2$-$D_3$ in place of $1\alpha,24(R)$-$(OH)_2$-$D_3$ in Example 2 to obtain a powdery injection preparation to be dissolved before use containing 1 $\mu$g of $1\alpha,25$-$(OH)_2$-$D_3$, 1 mg of EDTA, 5 mg of sodium ascorbate and 50 mg of mannitol in one vial.

EXAMPLE 4

The same procedure as in Example 2 was repeated by using $1\alpha,25$-$(OH)_2$-$D_3$-26,23-lactone in place of $1\alpha,24(R)$-$(OH)_2$-$D_3$ in Example 2 and also inositol in place of mannitol to obtain a powdery injection preparation to be dissolved before use containing 1 $\mu$g of $1\alpha,25$-$(OH)_2$-$D_3$-26,23-lactone, 1 mg of EDTA, 5 mg of sodium ascorbate and 50 mg of inositol in one vial.

EXAMPLE 5

A 0.1 mg amount of $1\alpha,25$-$(OH)_2$-$D_3$ was dissolved in 0.1 ml of ethanol (JP). This solution was added to a solution of 50 g of glycine dissolved in 1000 ml of distilled water for injection. After stirring, the mixture was filtered through a membrane filter and the filtrate was apportioned each in 1 ml into vials for lyophilization. The vials were lyophilized, filled internally with nitrogen gas, and then stoppered with sterilized rubber stoppers and caps made of aluminum, to obtain powdery injection preparations to be dissolved before use. The injection preparation obtained was found to contain 0.1 $\mu$g of $1\alpha,25$-$(OH)_2$-$D_3$ and 50 mg of glycine in one vial.

EXAMPLE 6

A 10 mg amount of $1\alpha,24(R)\text{-}(OH)_2\text{-}D_3$ was dissolved in 0.1 ml of ethanol (JP). This solution was added to a solution of 1 g of EDTA, 5 g of sodium ascorbate and 50 g of lactose dissolved in 1000 ml of distilled water for injection and, after stirring, filtered through a membrane filter. 0.5 ml of the filtrate was apportioned to each vial for lyophilization. The vials were lyophilized, filled internally with nitrogen gas and then stoppered with sterilized rubber stoppers and caps made of aluminum, to obtain powdery injection preparations to be dissolved before use. The injection preparation obtained was found to contain 5 µg of $1\alpha,24(R)\text{-}(OH)_2\text{-}D_3$, 0.5 mg of EDTA, 2.5 mg of sodium ascorbate and 25 mg of lactose in one vial.

EXAMPLE 7

A 1 mg amount of $1\alpha\text{-}OH\text{-}D_3$ was dissolved in 0.1 ml of ethanol (JP). This solution was added to a solution of 5 g of sodium carboxymethyl cellulose dissolved in 1000 ml of distilled water for injection. After stirring, the mixture was filtered through a membrane filter and the filtrate was apportioned each in 1 ml into vials for lyophilization. The vials were lyophilized, filled internally with nitrogen gas, and then stoppered with sterilized rubber stoppers and caps made of aluminum, to obtain powdery injection preparations to be dissolved before use. The injection preparation obtained was found to contain 1 µg of $1\alpha\text{-}OH\text{-}D_3$ and 5 mg of sodium carboxymethyl cellulose in one vial.

EXAMPLE 8

A 1 mg amount of $1\alpha\text{-}OH\text{-}D_3$ was dissolved in 0.1 ml of ethanol (JP). This solution was added to a solution of 5 g of ascorbic acid dissolved in 1000 ml of distilled water for injection. After stirring, the mixture was filtered through a membrane filter and the filtrate was apportioned each in 1 ml into vials for lyophilization. The vials were lyophilized, filled internally with nitrogen gas, and then stoppered with sterilized rubber stoppers and caps made of aluminum, to obtain powdery injection preparations to be dissolved before use. The injection preparation obtained was found to contain 1 µg of $1\alpha\text{-}OH\text{-}D_3$ and 5 mg of ascorbic acid in one vial.

EXAMPLE 9

A 1 mg amount of $1\alpha\text{-}OH\text{-}D_3$ was dissolved in 0.1 ml of ethanol (JP). This solution was added to a solution of 5 g of disodium hydrogenphosphate dissolved in 1000 ml of distilled water for injection. After stirring, the mixture was filtered through a membrane filter and the filtrate was apportioned each in 1 ml into vials for lyophilization. The vials were lyophilized, filled internally with nitrogen gas, and then stoppered with sterilized rubber stoppers and caps made of aluminum, to obtain powdery injection preparations to be dissolved before use. The injection preparation obtained was found to contain 1 µg of $1\alpha\text{-}OH\text{-}D_3$ and 5 mg of sodium monohydrogenphosphate in one vial.

EXAMPLE 10

A 1 mg amount of $1\alpha\text{-}OH\text{-}D_3$ was dissolved in 0.1 ml of ethanol (JP). This solution was added to a solution of 2.3 g of disodium hydrogenphosphate, 0.6 g of sodium dihydrogenphosphate, and 50 g of glycine dissolved in 1000 ml of distilled water for injection and after stirring, filtered through a membrane filter 1 ml of the filtrate was apportioned to each vial for lyophilization. The vials were lyophilized, filled internally with nitrogen gas, and then stoppered with sterilized rubber stoppers and caps made of aluminum, to obtain powdery injection preparations to be dissolved before use. The injection preparation obtained was found to contain 1 µg of $1\alpha\text{-}OH\text{-}D_3$, 50 mg of glycine, 2.3 mg of disodium hydrogenphosphate, and 0.6 mg of sodium dihydrogenphosphate in one vial.

EXAMPLE 11 (CONTROL)

The vials prepared in Examples 1 to 10 were stored at room temperature, while shielded from light, and the contents of the active type vitamins $D_3$ in the preparations were determined with the lapse of time. Simultaneously, 1 ml of an aqueous solution containing 1 µg of $1\alpha\text{-}OH\text{-}D_3$, 4.0 mg of Tween Polysorbate 20, 10.0 mg of sodium pyrosufite, and 1.0 mg of EDTA was filled into an ampoule replaced with nitrogen gas and the resultant aqueous injection preparation was stored as a control.

The changes in residual percentages, with the lapse of time, of the active type vitamins $D_3$ in Examples 1 to 10 and Example 11 (Control) are listed in Table 1.

As is clear from the results shown in Table 1, the preparations according to the present invention are extremely stable in comparison with the aqueous injection preparation of Example 11 (Control).

TABLE 1

| | Room Temperature (25° C.) | | |
|---|---|---|---|
| | 10 days | 20 days | 30 days |
| Example 1 | 100 | 100 | 100 |
| Example 2 | 100 | 100 | 100 |
| Example 3 | 99 | 99 | 100 |
| Example 4 | 100 | 99 | 100 |
| Example 5 | 100 | 100 | 100 |
| Example 6 | 100 | 100 | 100 |
| Example 7 | 100 | 99 | 98 |
| Example 8 | 99 | 99 | 100 |
| Example 9 | 100 | 99 | 100 |
| Example 10 | 100 | 100 | 100 |
| Example 11*[1] | 93 | 88 | 85 |

*[1]: Control

I claim:

1. A composition for injection of active vitamin $D_3$ comprising:
   a lyophilized product of at least one active vitamin $D_3$ selected from the group consisting of
   $1\alpha$-hydroxycholecalciferol,
   $1\alpha,25$-dihydroxycholecalciferol,
   $1\alpha,24$-dihydroxycholecalciferol,
   $1\alpha,25$-dihydroxycholecalciferol-26, 23-lactone; and
   100 to 1,000,000 parts by weight, based on 1 part by weight of said at least one active vitamin $D_3$, of at least one pharmaceutically acceptable excipient selected from the group consisting of amino acids, monosaccharides, disaccharides, ascorbic acid and acid salts thereof, citric acid and salts thereof, and sodium hydrogen phosphates.

2. A composition for injection of active vitamin $D_3$ as claimed in claim 1, wherein the excipient is glycine, arginine, alanine, manitol, inositol or xylitol.

3. A composition for injection of active vitamin $D_3$ as claimed in claim 1, wherein the excipient is an amino acid, monosaccharide, or disaccharide.